United States Patent [19]
Bakst

[11] Patent Number: 5,707,333
[45] Date of Patent: Jan. 13, 1998

[54] METHOD FOR REDUCING SENSATION IN A HUMAN BODY PART USING MAGNETISM

[76] Inventor: Alvin A. Bakst, 73-345 Highway 111, Suite 205, Palm Desert, Calif. 92260

[21] Appl. No.: 342,615

[22] Filed: Nov. 21, 1994

[51] Int. Cl.⁶ .................................................. A61N 2/08
[52] U.S. Cl. .................................................. 600/9; 600/15
[58] Field of Search .................. 128/898; 600/9–15

[56] References Cited

U.S. PATENT DOCUMENTS

| | | |
|---|---|---|
| 198,008 | 12/1877 | Edard . |
| 3,943,912 | 3/1976 | Nakayama . |
| 4,022,189 | 5/1977 | Boxer . |
| 4,162,672 | 7/1979 | Yazaki . |
| 4,480,596 | 11/1984 | Shumiyashu . |
| 4,587,956 | 5/1986 | Griffin et al. . |
| 5,312,321 | 5/1994 | Holcomb ................. 600/9 |
| 5,389,981 | 2/1995 | Riach, Jr. ................. 600/9 |

FOREIGN PATENT DOCUMENTS

| | | | |
|---|---|---|---|
| 0100050 | 2/1984 | European Pat. Off. ........... 600/15 |
| 0334141 | 9/1989 | European Pat. Off. ........... 600/15 |
| 27 33 982 | 2/1979 | Germany . |

OTHER PUBLICATIONS

Mansfield et al. "NMR Imaging in Biomedicine" Advances in Magnetic Resonance, pp. 297–332, Apr. 13 1992.

Lin et al. "Geophysical Variables nd Behavior: XXVII. Magnetic Necklace: Its Therapeutic Effectiveness on Neck and Shoulder Pain: 2. Psychological Assessment" Psychological Reports. pp. 639–649, Apr. 1985.

*Primary Examiner*—Jennifer Bahr
*Assistant Examiner*—Samuel Gilbert
*Attorney, Agent, or Firm*—Wood,Herron & Evans,L.L.P.

[57] ABSTRACT

Methods for preventing or reducing sensation originating in a part of a human body through the application of magnetic flux either to the lumbar-sacral region of the body or to the cervico-dorsal region of the body. For sensation originating in a part of the body at or below, but remote from, the lumbar-sacral region, a first method comprises placing at least one source of magnetic flux in close proximity to the lumbar-sacral region and allowing the source to remain there until the desired effect is achieved. For sensation originating in the upper extremities, a second method comprises placing at least one source of magnetic flux in close proximity to the cervico-dorsal region and allowing the source to remain there until the desired effect is achieved.

31 Claims, 2 Drawing Sheets

METHOD FOR REDUCING SENSATION IN A HUMAN BODY PART USING MAGNETISM

FIELD OF THE INVENTION

This invention relates to a method for preventing or reducing sensation in a part of a human body through the use of magnetic flux.

BACKGROUND OF THE INVENTION

Methods for treating pain in a human body through the use of magnetic flux have long been known. For example, it is known that magnetic bands covering the lower back can be effective in reducing pain originating in the lower back, and that a magnetic necklace covering the shoulders can reduce pain or stiffness originating in the shoulders. It is also known that the application of magnetic devices directly to the site of other painful body parts such as elbows or ankles can reduce pain in those parts.

These known methods all have the disadvantage of being purely local remedies effective only on the part of the body exposed to the magnetic flux. Such methods can be cumbersome in some cases. For instance, because magnetic treatment usually involves wearing a bulky and movement-restricting device on the painful body part for a substantial period of time, the treatment of pain in the joints by such methods is inconvenient, since the free movement of the joints is prevented. Furthermore, magnetic treatment devices are unsightly when used on parts of the body not covered by clothing. The known methods also have been limited to the treatment of pre-existing pain. They have not been shown to be effective in preventing the onset of pain.

It has been theorized in the prior art that a magnetic field may be capable of altering the electrical potential that exists across the outer fiber covering of all nerves. According to this theory, injury or trauma to body tissues causes the electrical potential across the coverings of nerves near the affected tissue to become more positive; the brain perceives such increased potential as pain. This theory and similar ones have led practitioners of the prior art to apply magnetic flux directly to the site of the injury or trauma, presumably in an attempt to reduce the electrical potential across the nerve covering and thereby reduce pain.

SUMMARY OF THE INVENTION

The present invention improves on the prior art by eliminating the requirement of wearing the magnetic treatment device directly at the site of the affected body part. The invention also improves on the prior art by providing a method for both reducing pre-existing sensations such as pain, and preventing the onset of such sensations before they start.

These improvements over the prior art are accomplished by taking advantage of the discovery that magnetic flux applied to the lumbar-sacral region of the body is effective in reducing or preventing the transmission of sensations to the brain from parts of the body at or below the lumbar-sacral region. Similarly, it has been discovered that application of magnetic flux to the cervico-dorsal region of the body is effective in reducing or preventing the transmission of sensations to the brain from the upper extremities of the body.

The theory of the present invention is different from theories explored in the prior art. The conduction of an impulse along a nerve is thought to be very similar to the conduction of electricity along a wire, in that both involve the flow of charged particles along the nerve or wire. In accordance with Lorentz's law, a charge moving in a magnetic field will be subjected to a deflecting force orthogonal to the direction of motion and the direction of magnetic flux. It is therefore believed that a magnet strong enough to deflect either positive or negative charge may, if placed in proximity to the course of a nerve, be capable of significantly altering or impairing the normal ionic flow along the nerve.

According to this theory, the magnetic flux need not be applied directly to the site at which the sensory impulse originates. Rather, the impulse may be altered or impaired at any point along the course of the nerve between the site where the impulse originates and its ultimate destination, the brain.

In the present invention, the lumbar-sacral region is selected as the point of application for sensory impulses originating at or below the lumbar-sacral region. This is a convenient location because it is the point at which all of the major nerves from the lower half of the body enter the spine on their way to the brain. Thus, application of magnetic flux at this point is effective in reducing or preventing sensation in any part of the body at or below the lumbar-sacral region.

Similarly, the cervico-dorsal region of the body is selected as the point of application for sensations originating in the upper extremities because it is the point at which all of the nerves from the upper half of the body enter the spine on their way to the brain. Thus, application of magnetic flux at this point is effective in reducing or preventing sensations originating in any part of the upper extremities.

The invention thereby eliminates the problems in the prior art with treating painful joints, hands, or feet, since unrestricted use of such parts is possible when wearing the belt or harness. Similarly, the invention solves the problem of unsightly treatment devices, because both the belt and harness may be worn under a shirt or blouse, hidden from view.

Thus, specifically for sensation originating at or below, but remote from, the lumbar-sacral region of the body, the method comprises the steps of (1) disposing at least one source of magnetic flux in close proximity to the lumbar-sacral region of the body, and (2) allowing the source of flux to remain so disposed for a period of time sufficient to prevent or reduce the sensation. For sensation originating in the upper extremities of the body, the method comprises the steps of (1) disposing at least one source of magnetic flux in close proximity to the cervico-dorsal region of the body, and (2) allowing the source of flux to remain so disposed for a period of time sufficient to prevent or reduce the sensation.

Although a single source of magnetic flux applied according to these methods is somewhat effective in reducing or preventing sensation, it has been found advantageous to use a plurality of such sources arranged by a supporting web into a planar array. The array of magnetic sources is of sufficient size and is so disposed as to cover substantially the entire lumbar-sacral region of the body, in the case of sensations originating in the lower half of the body. Likewise, the array is of sufficient size and is so disposed as to cover substantially the entire cervico-dorsal region of the body, in the case of sensations originating in the upper extremities. The array is then disposed in close proximity to either the lumbar-sacral or cervico-dorsal region and is allowed to remain so disposed for a period of time sufficient to prevent or reduce the sensation to be treated.

It has been found advantageous to orient each magnetic source in the array such that the north-south axis of the source is substantially perpendicular to the plane of the array. Furthermore, it has been found advantageous to orient the sources in the array such that all of the north poles of the sources face the same direction. Particularly good results have been achieved when the array is disposed such that all of the north poles face the body.

The supporting web for the lumbar-sacral array may be made a part of a belt that can be worn around the waist of a user, thereby holding the magnetic array in proper position over the lumbar-sacral region for as long a period as desired. Similarly, the supporting web for the cervico-dorsal array may be made a part of a harness that can be worn over the shoulders and around the upper torso of a user, thereby holding the magnetic array in proper position over the cervico-dorsal region for as long a period of time as desired. Both the belt and the harness may be worn under a shirt or blouse so that they are concealed from view.

The magnetic flux density, or strength, measured at the surface of each of the sources in the array has been found to be a critical factor. Little reduction in sensation has been achieved with source strengths of 800 Gauss or less. Preferably each should have a strength from about 1000 Gauss to about 5000 Gauss, and the magnets should collectively have a strength from about 10,000 Gauss to 75,000 Gauss, or more. Good results have been achieved with an array comprising 16 to 20 3800 Gauss magnets.

Permanent magnets made of ceramic or neodymium material are well suited for this invention. At the time of filing this application, approximately one-inch diameter, round 3800 Gauss ceramic permanent magnets could be obtained from Magnet Sales Manufacturing Company, Culver City, Calif. 90230.

BRIEF DESCRIPTION OF THE DRAWING

The aforementioned and other objects, advantages, and features of the invention will be better understood by reference to the following description and accompanying drawings, in which.

DETAILED DESCRIPTION OF SPECIFIC EMBODIMENTS

Figure 5:
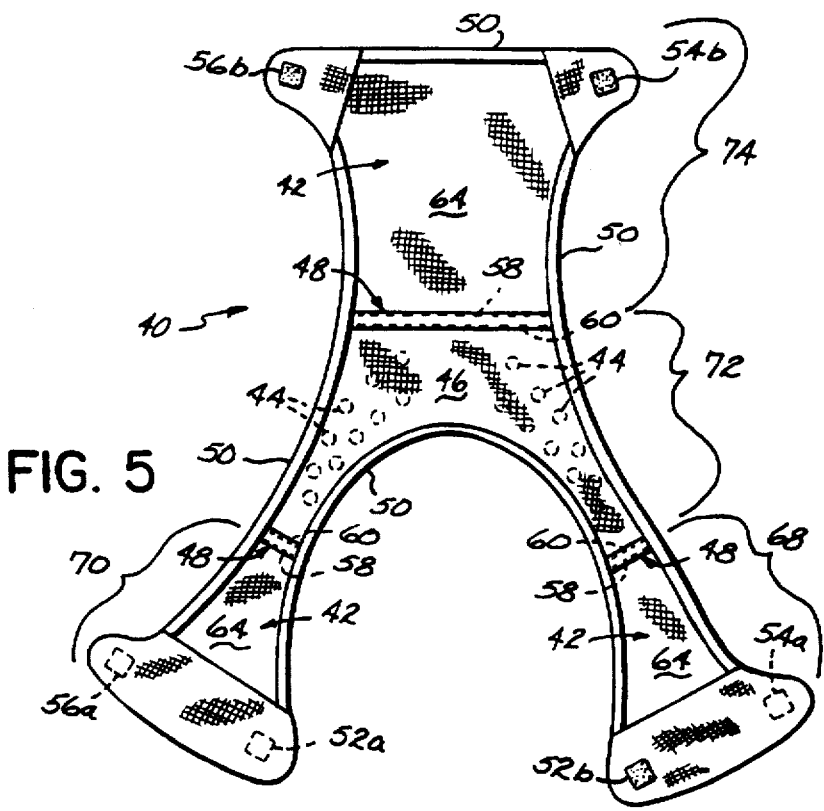
FIG. 5 depicts a harness that can be worn over the shoulders and around the upper torso of a user, the middle portion of the harness comprising of an array of magnetic sources arranged by a supporting web, which web forms an integral part of the harness.

Referring to FIGS. 1-4, magnetic belt 10 comprises an elastic supporting web 12, magnets 14, substantially inelastic bottomsheet 15 (see FIGS. 2 and 4) and topsheet 16, reinforcing patches 18, edge strips 20, and fastener members 22a and 22b. Magnets 14 are arranged in rows and columns on the inner surface 32 of wide center portion 24 of supporting web 12 and are affixed thereto by means of an adhesive or other suitable means. The magnets 14 are positioned such that their south-pole faces are in contact with inner surface 32 of supporting web 12, and their north-south axes are substantially perpendicular to supporting web 12. Thus, when the belt is worn with inner surface 32 of web 12 in contact with the user's body, the magnets 14 will all have their north poles directed toward the body. (The illustrated magnets have a square profile, however, the magnets may also be round, as seen in FIG. 5.)

Figure 1:
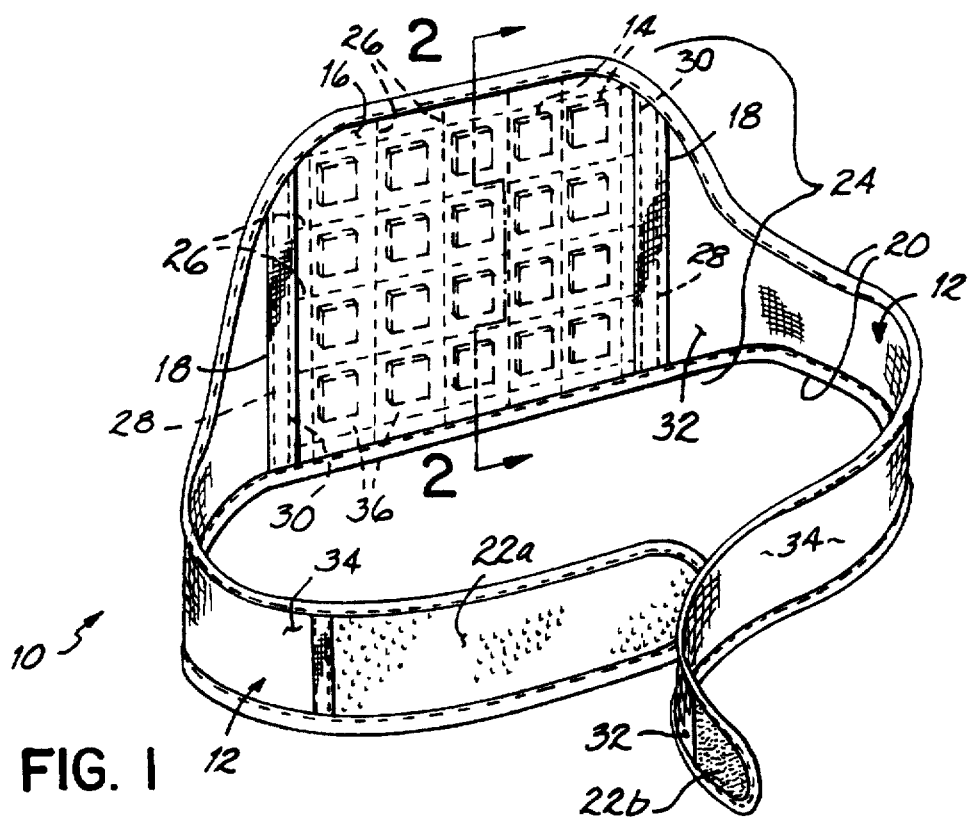
FIG. 1 shows a belt that can be worn around the waist of a user (as it appears when placed upright on a table in an orientation upside down from the orientation in which it is worn by a user), with the wide portion of the belt shown to comprise an array of magnetic sources arranged by a supporting web, which web forms an integral part of the belt.
Figures 2, 3, 4:
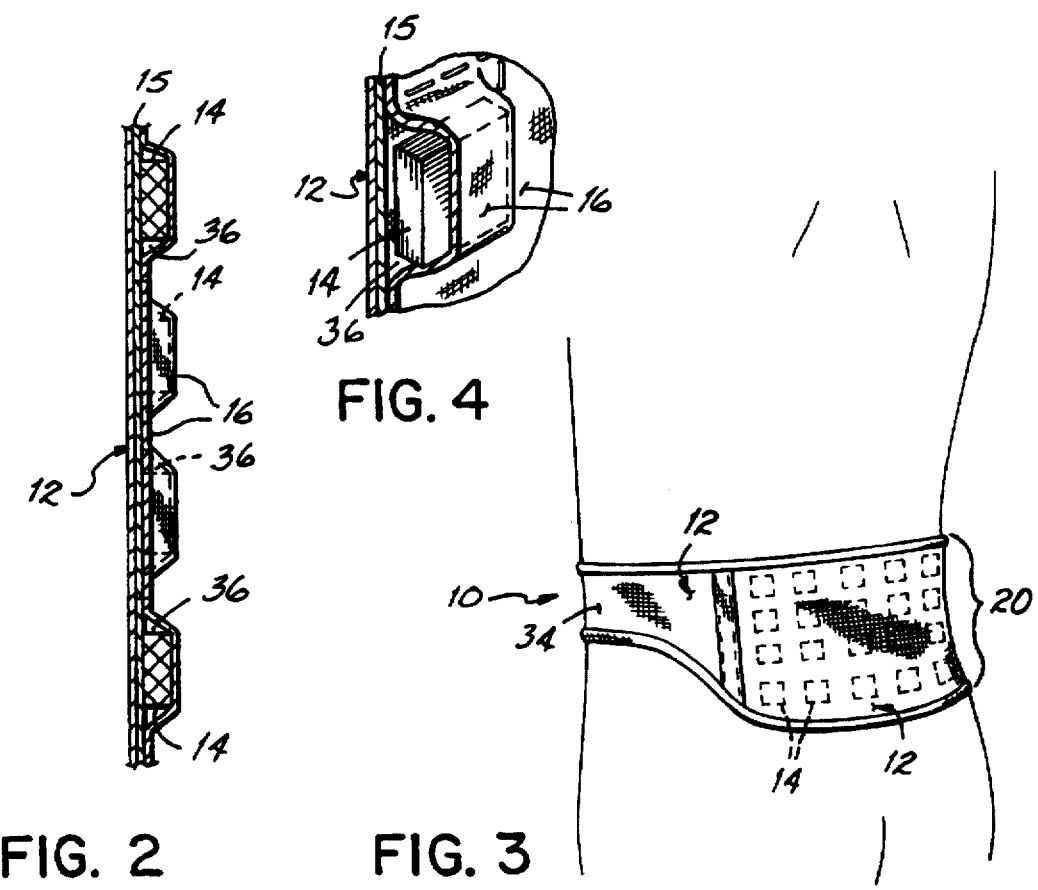
FIG. 2 shows a cross-sectional view through the magnetic array portion of the belt.
FIG. 3 shows the belt being worn by a user, with the magnetic array disposed so as to cover substantially the entire lumbar-sacral region of the user's body.
FIG. 4 is an enlarged view of a portion of the magnetic array, showing a single magnet contained within an individual pocket formed from the supporting web, bottomsheet and topsheet.

Topsheet 16 and bottomsheet 15 cover substantially the entire center portion 24 of supporting web 12, such that the magnets 14 are sandwiched between topsheet 16 and bottom sheet 15, as shown in FIG. 3. To construct the belt 10, magnets 14 are glued to bottomsheet 15 (which may be made of felt) to hold the magnets in place in an array. Then bottomsheet 15 and topsheet 16 are placed over supporting web 12, and topsheet 16 and bottomsheet 15 are stitched or otherwise affixed to supporting web 12 along the entire periphery of bottomsheet 15 and topsheet 16. Bottomsheet 15 and topsheet 16 are further stitched or otherwise affixed to supporting web 12 along lines 26 between the rows and columns of magnets 14, resulting in each magnet 14 being contained within an individual pocket 36 comprising a portion of bottomsheet 15 and a corresponding adjacent portion of topsheet 16, as shown in FIG. 4. The inelasticity of bottomsheet 15 and topsheet 16 serves to maintain magnets 14 in fixed positions relative to each other. This is important, as otherwise the attraction between the magnets would cause the belt to collapse into a ball, and the belt would be difficult to put on. Reinforcing patches 18 are stitched or otherwise affixed to supporting web 12 along lines 28 and to topsheet 16 and supporting web 12 along lines 30, so as to conceal the vertical stitched edges of bottomsheet 15 and topsheet 16.

Fastener members 22a and 22b are of a type generically known as the hook-and-loop type, but better known by the trademark "Velcro." Loop-type fastener member 22a is stitched or otherwise affixed to the outer surface 34 at one end of supporting web 12. Edge strips 20 are wrapped around the free edges of supporting web 12 and are stitched or otherwise affixed thereto, so as to produce a finished appearance and prevent fraying of the free edge. Hook-type fastener member 22b is then stitched or otherwise affixed to the inner surface 32 at the opposite end of supporting web 12. Loop type fastener member 22a is of a length sufficient to afford a reasonable range of adjustment of the size or circumference of the belt as worn, which adjustment is accomplished by attaching the hook-type fastener member 22b at different locations along the length of member 22a.

Snap fasteners can be suitably substituted for hook and loop fasteners 22, for example a female snap fastener in the place of hook fastener 22b can be mated to a number of male snap fasteners arranged in a row in the place of loop fastener 22a. Snap fasteners may be more easily manufacturable than hook and loop fasteners. Other kinds of clothing fasteners (e.g., buttons and buttonholes) may also be used.

According to the method of the invention, a user desiring to prevent or reduce sensation originating at or below, but remote from, the lumbar-sacral region of the body positions belt 10 as shown in FIG. 3 with the outer surface 34 of web 12 facing outward. Fastener members 22a and 22b are engaged to afford a snug but comfortable fit. The belt is then left in position until the desired therapeutic effect is achieved.

The magnetic harness is described with reference to FIGS. 5–7. Its construction is similar to that of the belt 10 of FIGS. 1–4. Harness 40 comprises an elastic supporting web 42, magnets 44, a substantially inelastic bottomsheet (not shown) and topsheet 46, reinforcing patches 48, edge strips 50, and fastener members 52a and 52a, 54a and 54b, and 56a and 56b. Supporting web 42 has inner surface 64 and outer surface 66. Harness 40 has right breast portion 68, left breast portion 70, center portion 72, and rear portion 74.

Magnets 44 are arranged in a suitable pattern on inner surface 64 of center portion 72 and are affixed thereto by means of an adhesive or other suitable means. The magnets are positioned such that their south-pole faces are in contact with inner surface 64 of supporting web 42 and their north-south axes are substantially perpendicular to supporting web 42. Thus, when the harness is worn with inner surface 64 in contact with a user's body, magnets 44 will all have their north poles directed toward the body.

The bottomsheet (not shown) and topsheet 46 cover substantially the entire center portion 72 such that magnets 44 are sandwiched between the bottomsheet and topsheet 46, similar to the construction of the magnetic array shown in FIG. 4. The bottomsheet and topsheet 46 are stitched or otherwise affixed to supporting web 42 along their entire periphery, and are further stitched or otherwise attached to supporting web 42 in such a manner that each magnet 44 is contained within an individualized pocket comprising a portion of the bottomsheet and a corresponding adjacent portion of topsheet 46. Reinforcing patches 48 are stitched or otherwise affixed to supporting web 42 along lines 58 and to topsheet 46 and supporting web 42 along lines 60, so as to conceal the stitched edges of topsheet 46. Edge strips 50 are wrapped around the free edges of supporting web 42 and are stitched or affixed thereto, so as to produce a finished appearance and prevent fraying of free edges.

Loop-type fastener member 52a is affixed to outer surface 66 approximately on the lowermost right-hand edge of left breast portion 70. Corresponding hook-type fastener member 52b is affixed to inner surface 64 approximately on the lowermost left-hand edge of right breast portion 68. Loop-type fastener member 54a is affixed to outer surface 66 approximately on the lowermost right-hand edge of right breast portion 68. Corresponding hook-type fastener member 54b is affixed to inner surface 64 approximately on the uppermost right-hand edge of rear portion 74. Loop-type fastener member 56a is affixed to outer surface 66 approximately on the lowermost left-hand edge of left breast portion 70. Corresponding hook-type fastener member 56b is affixed to inner surface 64 approximately on the uppermost left-hand edge of rear portion 74.

Loop-type fastener members 52a, 54a, and 56a may be made of sufficient size as to afford a reasonable range of size adjustment for the harness. Such adjustment is accomplished by attaching corresponding hook-type fastener members 52a, 54b, and 56b at different locations on loop-type members 52a, 54a, and 56a.

Again, snap fasteners, or other fasteners such as buttons and buttonholes, may be substituted for hook-and-loop fasteners for easier manufacture.

Figure 6:
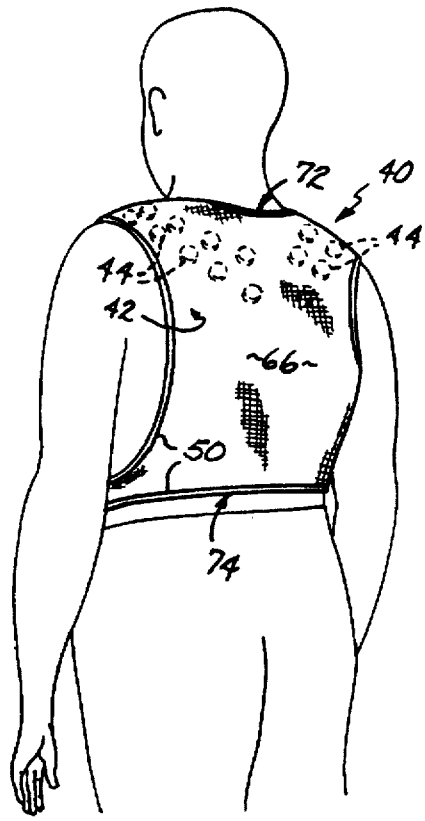
FIG. 6 is a view from behind showing the harness being worn by a user, with the magnetic array shown to cover substantially the entire cervico-dorsal region of the user's body.
Figure 7:
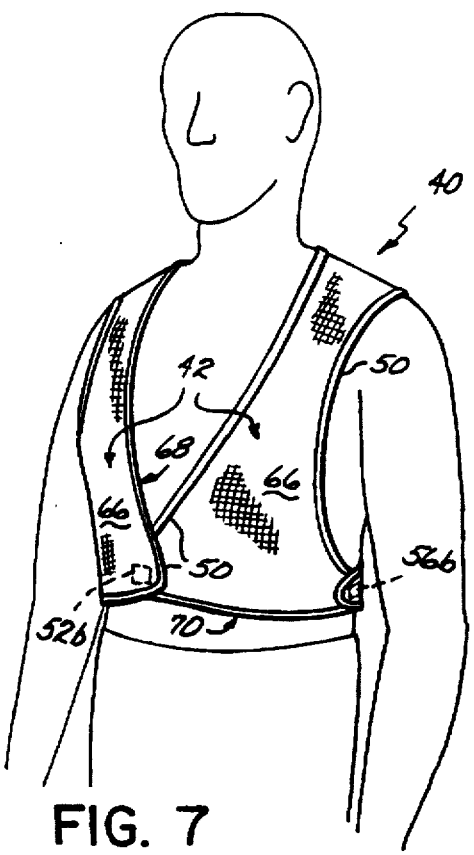
FIG. 7 is a view from the front showing the harness being worn.

A user desiring to prevent or reduce sensation originating in the upper extremities positions harness 40 as shown in FIG. 6 with outer surface 66 facing outward. Fastener members 52a and 52a, 54a and 54b, and 56a and 56b are engaged to afford a snug but comfortable fit, as shown in FIG. 7. The harness is then left in position until the desired therapeutic effect is achieved.

In experiments conducted by the inventor, patients experiencing ankle pain have reported that wearing the magnetic belt produced a marked reduction in pain within 24 to 48 hours.

The belt is also particularly beneficial in preventing the pain associated with premenstrual syndrome (PMS). Patients have reported substantial reduction in PMS lower back pain through use of the belt. Although such pain is perceived as lower back pain, it is thought that it actually originates elsewhere. It is to be noted that the parasympathetic nerves from the pelvic area enter the spine in the lumbar-sacral region. Thus, it is believed that application of magnetic flux to the lumbar-sacral region has a beneficial effect on PMS lower back pain even though the pain actually does not originate in the lower back.

In the case of PMS symptoms, the belt has the further advantage of providing a preventive treatment. Because most women who experience PMS lower back pain are able to predict with some certainty when their back pain will begin each month, it is possible for them to begin wearing the belt before the pain starts, and thereby prevent the sensation of pain from being experienced in undiminished intensity.

The particular apparatus shown for use in practicing the invention disclosed herein is for illustrative purposes only, and is not intended to define the full scope of the invention. Persons skilled in the art may make numerous changes in details of construction and arrangement of parts of the disclosed apparatus without departing from the scope of the invention, which scope is to be determined by reference to the following claims.

What is claimed is:

1. A method for reducing transmission in a human body of sensation from a body part to the brain, said sensation originating in said body part, said body part being located below and remote from the lumbar-sacral region of the body, the method comprising the steps of:
   a) disposing at least one source of magnetic flux in close proximity to the lumbar-sacral region of the body; and
   b) allowing said source to remain so disposed for a period of time sufficient to reduce transmission of said sensation from said body part to the brain.

2. The method of claim 1 wherein there are multiple said sources having combined magnetic flux density from substantially 10,000 Gauss to substantially 75,000 Gauss.

3. The method of claim 1 wherein said source has a north-south magnetic axis and is disposed such that said north-south magnetic axis is substantially perpendicular to the surface of the body in the lumbar-sacral region.

4. The method of claim 3 wherein said source has a north pole which is directed toward the lumbar-sacral region.

5. The method of claim 1 wherein a plurality of sources are arranged into an array by a supporting web having a smoothly curved inner surface, each said source having a north-south magnetic axis oriented substantially perpendicular to said inner surface of said web, said array being disposed such that said inner surface is substantially parallel to the surface of the body in the lumbar-sacral region.

6. The method of claim 5 wherein each said source in said array has a north pole directed toward the lumbar-sacral region of the body.

7. The method of claim 6 wherein said sources have a combined magnetic flux density from substantially 10,000 Gauss to substantially 75,000 Gauss.

8. The method of claim 7 wherein each said source is a ceramic permanent magnet.

9. The method of claim 7 wherein each said source is a neodymium permanent magnet.

10. The method of claim 1 wherein said sensation is of pain.

11. The method of claim 10 wherein said pain is pain associated with pre-menstrual syndrome.

12. A method for reducing transmission in a human body of sensation from a body part to the brain, said sensation originating in said body part, said body part being located in the upper extremities of the body, the method comprising the steps of:
 a) disposing at least one source of magnetic flux in close proximity to the cervico-dorsal region of the body; and
 b) allowing said source to remain so disposed for a period of time sufficient to reduce transmission of said sensation from said body part to the brain.

13. The method of claim 12 wherein there are multiple said sources having a combined magnetic flux density from substantially 10,000 Gauss to substantially 75,000 Gauss.

14. The method of claim 12 wherein said source has a north-south magnetic axis and is disposed such that said north-south magnetic axis is substantially perpendicular to the surface of the body in the cervico-dorsal region.

15. The method of claim 14 wherein said source has a north pole which is directed toward the cervico-dorsal region.

16. The method of claim 12 wherein a plurality of said sources are arranged into an array by a supporting web having a smoothly curved inner surface, each said source having a north-south magnetic axis oriented substantially perpendicular to said inner surface of said web, said array being disposed such that said inner surface is substantially parallel to the surface of the body in the cervico-dorsal region.

17. The method of claim 16 wherein each said source in said array has a north pole directed toward the cervico-dorsal region of the body.

18. The method of claim 17 wherein said sources have a combined magnetic flux density from substantially 10,000 Gauss to substantially 75,000 Gauss.

19. The method of claim 18 wherein each said source is a ceramic permanent magnet.

20. The method of claim 18 wherein each said source is a neodymium permanent magnet.

21. The method of claim 12 wherein said sensation is of pain.

22. The method of claim 1 wherein said sensation is perceived to be originating in the lumbar-sacral region of the body.

23. A method for reducing transmission in a human body of sensation along a course of a nerve from a body part to the brain, said course extending from said body part to the brain, said sensation originating in said body part, the method comprising the steps of:
 a) disposing at least one source of magnetic flux in close proximity to a point along said course remote from said body part between said body part and the brain; and
 b) allowing said source to remain so disposed for a period of time sufficient to reduce transmission of said sensation from said body part to the brain.

24. A method for reducing transmission in a human body of sensation from a body part to the brain, said sensation originating and perceived to be originating in said body part, said body part being located at or below the lumbar-sacral region of the body, the method comprising the steps of:
 a) disposing at least one source of magnetic flux in close proximity to the lumbar-sacral region of the body; and
 b) allowing said source to remain so disposed for a period of time sufficient to reduce transmission of said sensation from said body part to the brain.

25. The method of claim 24 wherein there are multiple said sources having combined magnetic flux density from substantially 10,000 Gauss to substantially 75,000 Gauss.

26. The method of claim 25 wherein each said source has a north-south magnetic axis and a north pole and is disposed such that said magnetic axis is substantially perpendicular to the surface of the body in the lumbar-sacral region with the north pole directed toward the lumbar-sacral region.

27. The method of claim 25 wherein said sources are arranged into an array by a supporting web having a smoothly curved inner surface, each said source having a magnetic axis oriented substantially perpendicular to said inner surface, said array being disposed with said inner surface substantially parallel to the surface of the body in the lumbar-sacral region.

28. A method for reducing transmission in a human body of sensation from a body part to the brain, said sensation originating and perceived to be originating in said body part, said body part being located in the upper extremities of the body, the method comprising the steps of:
 a) disposing at least one source of magnetic flux in close proximity to the cervico-dorsal region of the body; and
 b) allowing said source to remain so disposed for a period of time sufficient to reduce transmission of said sensation from said body part to the brain.

29. The method of claim 28 wherein there are multiple said sources having combined magnetic flux density from substantially 10,000 Gauss to substantially 75,000 Gauss.

30. The method of claim 29 wherein each said source has a north-south magnetic axis and a north pole and is disposed such that said magnetic axis is substantially perpendicular to the surface of the body in the cervico-dorsal region with the north pole directed toward the cervico-dorsal region.

31. The method of claim 30 wherein said sources are arranged into an array by a supporting web having a smoothly curved inner surface, each said source having the magnetic axis oriented substantially perpendicular to said inner surface, said array being disposed with said inner surface substantially parallel to the surface of the body in the cervico-dorsal region.

* * * * *

UNITED STATES PATENT AND TRADEMARK OFFICE
CERTIFICATE OF CORRECTION

PATENT NO.   : 5,707,333
DATED        : January 13, 1998
INVENTOR(S)  : Alvin A. Bakst It is certified that error appears in the above-identified patent and that said Letters Patent is hereby corrected as shown below:

Column 5, Line 6, delete "and 52a", insert --and 52b--.

Column 5, line 55, delete "52a", insert --52b--.

Column 5, line 64, delete "and 52a", insert --and 52b--.

Column 8, line 27, Claim 27, delete "axis oriented", insert --axis which is oriented--.

Signed and Sealed this

Eighteenth Day of May, 1999

Attest:

Q. TODD DICKINSON

*Attesting Officer*   Acting Commissioner of Patents and Trademarks